US012419989B2

(12) United States Patent
Sherman et al.

(10) Patent No.: US 12,419,989 B2
(45) Date of Patent: *Sep. 23, 2025

(54) SOLID SOLUTION COMPOSITIONS COMPRISING CANNABIDIOLS

(71) Applicant: Medtronic Xomed, Inc., Jacksonville, FL (US)

(72) Inventors: Ethan G. Sherman, Jacksonville, FL (US); Wei Chen, St. Johns, FL (US); Denise E. Guenther, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 7 days.

This patent is subject to a terminal disclaimer.

(21) Appl. No.: 18/513,436

(22) Filed: Nov. 17, 2023

(65) Prior Publication Data

US 2024/0082456 A1    Mar. 14, 2024

Related U.S. Application Data

(63) Continuation of application No. 17/360,691, filed on Jun. 28, 2021, now Pat. No. 11,839,693, which is a continuation of application No. 16/706,209, filed on Dec. 6, 2019, now Pat. No. 11,045,577, which is a continuation of application No. 15/954,471, filed on Apr. 16, 2018, now Pat. No. 10,517,986, which is a continuation of application No. 14/962,493, filed on Dec. 8, 2015, now abandoned.

(51) Int. Cl.

| | | |
|---|---|---|
| *A61L 24/00* | (2006.01) | |
| *A61F 13/20* | (2006.01) | |
| *A61K 9/00* | (2006.01) | |
| *A61L 2/00* | (2006.01) | |
| *A61L 15/22* | (2006.01) | |
| *A61L 24/04* | (2006.01) | |
| *A61L 24/08* | (2006.01) | |
| *A61L 31/04* | (2006.01) | |
| *A61L 31/14* | (2006.01) | |
| *A61L 31/16* | (2006.01) | |
| *B65B 55/16* | (2006.01) | |
| *B65B 63/08* | (2006.01) | |

(52) U.S. Cl.
CPC ...... *A61L 24/0042* (2013.01); *A61F 13/2005* (2013.01); *A61K 9/0043* (2013.01); *A61L 2/0029* (2013.01); *A61L 15/225* (2013.01); *A61L 24/0015* (2013.01); *A61L 24/0036* (2013.01); *A61L 24/043* (2013.01); *A61L 24/08* (2013.01); *A61L 31/042* (2013.01); *A61L 31/146* (2013.01); *A61L 31/148* (2013.01); *A61L 31/16* (2013.01); *B65B 55/16* (2013.01); *B65B 63/08* (2013.01); *A61L 2202/24* (2013.01); *A61L 2300/232* (2013.01); *A61L 2300/404* (2013.01); *A61L 2400/04* (2013.01)

(58) Field of Classification Search
CPC . A61F 13/2005; A61K 9/0043; A61L 2/0029; A61L 15/225; A61L 24/08; A61L 24/0036; A61L 24/0015; A61L 24/0042; A61L 24/043; A61L 31/16; A61L 31/148; A61L 31/146; A61L 31/042; A61L 2202/24; A61L 2300/404; A61L 2300/232; A61L 2400/04; B65B 63/08; B65B 55/16
USPC .......................................................... 514/55
See application file for complete search history.

(56) References Cited

U.S. PATENT DOCUMENTS

| | | |
|---|---|---|
| 7,993,675 B2 | 8/2011 | Oliver et al. |
| 8,313,762 B2 | 11/2012 | Oliver et al. |
| 8,530,632 B2 | 9/2013 | Tijsma et al. |
| 8,668,703 B2 | 3/2014 | Sullivan et al. |
| 8,802,652 B2 | 8/2014 | Myntti et al. |
| 8,920,715 B2 | 12/2014 | Roberts et al. |
| 9,061,087 B2 | 6/2015 | Roberts et al. |
| 9,205,049 B2 | 12/2015 | Reddy et al. |
| 9,649,482 B2 | 5/2017 | Roberts et al. |
| 10,517,986 B2 * | 12/2019 | Sherman ............... A61L 31/148 |
| 11,045,577 B2 * | 6/2021 | Sherman ................ A61P 43/00 |
| 11,839,693 B2 * | 12/2023 | Sherman ................ A61L 31/16 |
| 2005/0147658 A1 | 7/2005 | Tapolsky et al. |
| 2007/0104769 A1 | 5/2007 | Feng et al. |
| 2007/0254016 A1 | 11/2007 | Andersen et al. |
| 2007/0264310 A1 | 11/2007 | Hissong et al. |
| 2009/0291911 A1 | 11/2009 | Myntti et al. |
| 2010/0178313 A1 | 7/2010 | Larsen et al. |
| 2010/0239632 A1 | 9/2010 | Walsh |
| 2011/0052663 A1 | 3/2011 | Roberts |
| 2014/0323433 A1 | 10/2014 | Myntti et al. |

(Continued)

FOREIGN PATENT DOCUMENTS

| | | |
|---|---|---|
| JP | 2003159528 A | 6/2003 |
| WO | 03020771 A1 | 3/2003 |

OTHER PUBLICATIONS

Canadian Examiner's Report for application No. 3,006,565 dated Nov. 17, 2022.

(Continued)

*Primary Examiner* — Yih-Horng Shiao

(74) *Attorney, Agent, or Firm* — Carter, DeLuca & Farrell LLP

(57) ABSTRACT

An implantable article comprising a dissolvable sponge derived from the mixture of chitosan, a first polysaccharide and a second polysaccharides. The polysaccharides have different number average molecular weight characteristics to enable the control of the mechanical features of the sponge.

20 Claims, 2 Drawing Sheets

(56) References Cited

U.S. PATENT DOCUMENTS

2016/0184564 A1  6/2016  Spearman et al.
2017/0157283 A1  6/2017  Sherman et al.

OTHER PUBLICATIONS

Casettari et al., "Chitosan in nasal delivery systems for therapeutic drugs," *Journal of Controlled Release*, 190(204): 189-200, Available online May 10, 2014.
International Preliminary Report on Patentability for International Application No. PCT/US2018/064234, dated Jun. 21, 2018 (9 pages).
U.S. Appl. No. 14/962,493, filed Dec. 8, 2015, Inventor(s): Sherman et al.
501(k) Summary: PosiSep T N' and PosiSep TM X Hemostat Dressing/Intranasal Splint, Hemostasis, LLC, Mar. 27, 2013, 5 pages.
Office Action for Japanese Application No. 2018-530136, dated Nov. 24, 2020, 7 pages.

\* cited by examiner

SOLID SOLUTION COMPOSITIONS COMPRISING CANNABIDIOLS

CROSS-REFERENCE TO RELATED APPLICATION

This application is a continuation of U.S. patent application Ser. No. 17/360,691 filed Jun. 28, 2021 which is a continuation of U.S. patent application Ser. No. 16/706,209 filed Dec. 6, 2019 now granted as U.S. Pat. No. 11,045,577, entitled DISSOLVABLE NASAL SINUS SPONGE, which is a continuation of U.S. patent application Ser. No. 15/954,471 filed Apr. 16, 2018, now granted as U.S. Pat. No. 10,517,986 entitled DISSOLVABLE NASAL SINUS SPONGE, which is a continuation of U.S. patent application Ser. No. 14/962,493 filed Dec. 8, 2015, now abandoned, entitled DISSOLVABLE NASAL SINUS SPONGE, the entire disclosures of all of which are incorporated herein by reference.

FIELD OF THE INVENTION

This invention relates to dissolvable sponges or stents that are used in or on tissue and structures in the nasal passages or other parts of the anatomy.

BACKGROUND

Nasal packing and sponges (stents) are used to hold open the nasal cavity (stenting), to absorb fluid or blood and to prevent adhesions within the sinus cavity after sinus surgery. A recognized issue with conventional nasal stents currently on the market is that they have to be removed after surgery. Removal of the nasal stent can cause pain for the patient and result in scarring or re-bleeding. In addition, those conventional stents that are dissolvable, or fragmentable, may not provide any therapeutic benefit and as a result may cause infection due to the specific materials used in the stent.

SUMMARY

This disclosure is directed to an implantable article comprising a dissolvable sponge derived from the mixture of chitosan, a first polysaccharide and a second polysaccharide. The polysaccharides of the mixture are not a chitosan, or a derivative thereof, and they also have differing number average molecular weights. In that regard, the first polysaccharide and the second polysaccharide may be the same or different polysaccharides. The resulting dissolvable sponge may be packaged and sold in compressed form, may be trimmed to a desired size or shape for implantation at a treatment site, and may be rehydrated prior to or following implantation. Embodiments of this disclosure may control bleeding, prevent adhesions, aid in wound healing, provide antibacterial effectiveness, and absorb drainage. Following the implantation at a treatment site, the sponge can be absorbed by the body or it can also just dissolve away either mechanically, for example by reduction in mechanical strength, or chemically, for example by reduction in the number average molecular weight. The dissolution of the sponge eliminates the need for painful nasal packing removal and secondary post-op procedures.

In certain embodiments of this disclosure, the dissolvable sponge is a mixture derived from chitosan, a first polysaccharide and a second polysaccharide. The use of two polysaccharides having different number average molecular weight characteristics enables the control of the mechanical features of the sponge. One of ordinary skill in the art with knowledge of this disclosure can select the amounts of chitosan and polysaccharides to achieve desired stenting characteristics while also formulating an appropriate dissolution rate over time.

In accordance with this disclosure, a first polysaccharide is selected that possesses a number average molecular weight of 1.3 million or greater. The first polysaccharide is combined with a second polysaccharide having a number average molecular weight of 500,000 to less than 1.3 million. The resulting dissolvable sponge exhibits one or more of a wet compression strength or a dry compression strength of at least 20 g according to the Compression Test. The dry compression strength is an indication of the sponge's ability to remain in a pliable state for subsequent use without tearing, breaking or flaking. The wet compression strength is an indication of the sponge's ability to maintain its shape or form in application and thereby achieve a desirable level of stenting.

The invention provides in another aspect a method for making an implantable article, which comprises providing a solution containing a chitosan, a first polysaccharide and a second polysaccharide, freezing the solution, lyophilizing the solution to form a sponge, packaging the sponge in a sealed package and sterilizing the sponge, the method thereby forming an implantable article suitable for use as a dissolvable sponge when rehydrated.

The invention provides in another aspect a method for treating tissue and other body structures, which method comprises applying thereto a sponge comprising a chitosan, a first polysaccharide and a second polysaccharides, wherein the polysaccharides having different number average molecular weights.

DETAILED DESCRIPTION

The following detailed description describes certain embodiments and is not to be taken in a limiting sense. All weights, amounts and ratios herein are by weight, unless otherwise specifically noted. The terms shown below have the following meanings:

The term "adhesion" refers to the sticking together of a body structure or prosthetic material to tissue, to the sticking together of tissue to tissue with which it is in intimate contact for extended periods, or to the formation of tissue that connects body structures, prosthetic materials or tissues to one another across a normally open space.

"antimicrobial" refers to an ability to cause greater than a 90% numeric reduction (viz., at least a 1-log order reduction) in a population of one or more of *Staphylococcus aureus, Pseudomonas aeruginosa, Streptococcus pneumonia, Haemophilus influenzae, Moraxella catarrhalis, Staphylococcus epidermidis, Escherichia coli, Citrobacter freundii, Enterobacter aerogenes, Klebsiella pneumonia, Proteus mirabilis, Serratia marcescens, Staphylococcus saprophyticus, Micrococcus luteus, Streptococcus mutans, Corynebacterium diphtheria*, or *Corynebacterium tuberculostearicum*.

"dissolvable" when used in reference to a substance means that the substance is capable of being absorbed by the body or broken down or passed into solution such as by mechanical action or chemical action.

"fluid" when used in reference to a substance means that the substance is a liquid having a loss modulus (G") greater than its storage modulus (G') and a loss tangent (tan δ) greater than 1.

"gel" when used in reference to a substance means that the substance is deformable (viz., is not a solid), G" is less than G' and tan δ is less than 1.

"hydrated" when used in reference to a device or substance of this disclosure means that the device or substance contains water via absorption. A "fully hydrated" device or substance is incapable of taking up additional water of hydration. A "partially hydrated" device or substance is capable of taking up additional water of hydration.

"mucoadhesive" means that the substance or device adheres to the mucus covering epithelia.

"nasal or sinus cavities" refers to the various tissues defining the normally air-filled passages and chambers within the nose and sinus including but not limited to the nostrils or nares, the nasal concha or turbinates, the frontal, ethmoid, sphenoid and maxillary sinuses, the sinus ostia and the nasopharnyx.

"polysaccharide" includes derivatives of polysaccharides and modified polysaccharides, as well as derivatives of individual polysaccharide species and modified individual polysaccharide species. For example, the term "hydroxyethyl cellulose" includes hydroxyethyl cellulose derivatives and modified hydroxyethyl cellulose.

Figure 1:
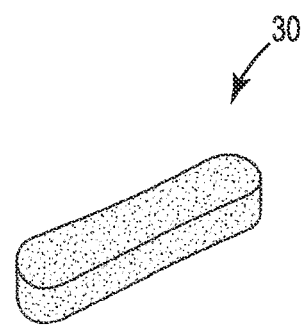
FIG. 1 is a perspective view of the disclosed sponge.
Figure 2:
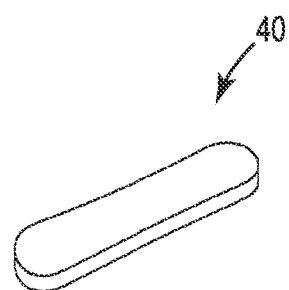
FIG. 2 is a perspective view of the disclosed sponge in a compressed state.

FIG. 1 shows an example 30 of the disclosed sponge in an uncompressed state, and FIG. 2 shows an example 40 of the disclosed sponge in a compressed state. In its uncompressed form prior to hydration, sponge 30 provides an essentially anhydrous porous polysaccharide matrix formed from chitosan and two or more polysaccharides different than chitosan. A compressed sponge such as sponge 40 may be formed using a variety of techniques including a press with opposing platens, calendaring rollers, a plastic bag subjected to external air pressure or internal vacuum, and other compression techniques that may be envisioned by persons having ordinary skill in the art. Either the compressed or uncompressed forms of the disclosed sponge may be employed in medical procedures. Before placing a sponge such as sponge 30 or sponge 40 in a treatment site, the sponge may be trimmed to a desired size or shape (using, for example, a suitable punch and die if trimming is done at a manufacturing site, or scissors or a scalpel if trimming is done at the time of placement). The untrimmed or trimmed sponge may then be hydrated. If previously compressed, the sponge may be allowed to expand before, during or after insertion into the treatment site.

Embodiments of the dissolvable sponge of this disclosure include a mixture of chitosan, a first polysaccharide and a second polysaccharide. The polysaccharides of the mixture are not a chitosan, or a derivative thereof, and they also have different number average molecular weights. Since the molecular weights are different, certain embodiments may utilize the same polysaccharide as both the first polysaccharide and the second polysaccharide.

The combination of components such as chitosan, a first polysaccharide and second polysaccharide enables the design and control of the mechanical features of the sponge. For example, the resulting dissolvable sponge has compression strength values, both dry and wet, that enable a desirable level of stenting. The designed mechanical features are selected to maintain the sponge in its physical form during positioning in a nasal cavity without tearing, breaking or flaking. However, the mechanical features do not adversely impact the sponge on initial application and when in place in a nasal cavity do not hinder natural drainage through the nasal cavity. Additionally, the dissolvable sponge, when at least partially hydrated is mucoadhesive and thereby holds the sponge in place for a desired time period until it dissolves.

Chitosan is a polysaccharide employed (together with the first and second polysaccharides) as one of the components useful in forming the disclosed dissolvable sponge. Chitosan includes derivatives of chitosan and modified chitosan. Non-limiting examples of chitosan and its salts (including citrate, nitrate, lactate, phosphate, chloride and glutamate salts) may be obtained from a variety of commercial sources including KitoZyme S.A., Fluka Chemie AG, the NovaMatrix unit of FMC BioPolymer AS, Heppe Medical Chitosan GmbH and Sigma-Aldrich Co. Chitosan may also be synthesized by elimination of N-acetyl groups through deacetylation of chitin (poly-N-acetyl-D-glucosamine) by hydrolysis. The resulting oligomer or polymer has a plurality of repeating units (e.g., about 2 to about 10,000 repeating units, about 60 to about 600 repeating units, or such other amount as may be desired for the chosen end use). Some or all of the repeating units will contain deacetylated amino groups (e.g., about 30 to about 100% or about 60 to about 100% of the total repeating units), with the remaining repeating units (if any) containing acetylated amino groups. Chitosan is a cationic polymer composed of glucosamine monomers, and may have a variety of number average molecular weights, e.g., about 400 to about 2000 kDa, about 10 to about 500 kDa, or about 10 to about 100 kDa. The chitosan may for example be an ultralow molecular weight material having a number average molecular weight less than about 50 kDa, a low molecular weight material having a number average molecular weight of about 50 to about 200 kDa, a medium molecular weight material having a number average molecular weight of about 200 to about 500 kDa or a high molecular weight material having a number average molecular weight greater than about 500 kDa.

Chitosan derivatives may also be employed, for example derivatives in which one or more hydroxyl or amino groups have been modified for the purpose of altering the solubility or mucoadhesion characteristics of the derivative. Exemplary derivatives include thiolated chitosans, and non-thiolated chitosan derivatives such as carboxymethyl, acetylated, alkylated or sulfonated chitosans (for example O-alkyl ethers, O-acyl esters, cationized trimethyl chitosans and chitosans modified with polyethylene glycol). Chitosan derivatives may be obtained from a variety of sources. For example, thiolated chitosans may be obtained from ThioMatrix Forschungs Beratungs GmbH and Mucobiomer Biotechnologische Forschungs-und Entwicklungs GmbH or prepared by reaction of chitosan with a suitable thiolating reactant, e.g., as described in Published PCT Application No. WO 03/020771 A1.

A particular chitosan derivative well suited in some embodiments for the formation and application of a dissolvable sponge is chitosan hydrochloride. Chitosan hydrochloride at pH below 6.6 (acidic environment) provides antibacterial properties and therefore adds additional efficacy to the dissolvable sponge incorporating this particular chitosan derivative. The electrostatic forces of the positive charged chitosan in an acidic environment (pH≤6.6) are attracted to the negative charged bacterial cell membrane wall. This charge interaction prevents the bacteria from replicating providing a level of antibacterial effectiveness. An example of commercially available chitosan hydrochloride is chitosan HCl available from Heppe Medical Chitosan GmbH, Halle, Germany.

The first and second polysaccharides that form the dissolvable sponge within chitosan may be different or the same polysaccharides with varying number average molecular weights. Non-limiting examples include celluloses, agars, alginates, carrageenans, chitins, chondroitin sulfates, dextrans, galactomannans, glycogens, hyaluronic acids, starches, celluloses, and other biocompatible polysaccharides capable of being formed into a dissolvable sponge. Derivatives (including oxidized polysaccharides and salts) and mixtures of polysaccharides (including derivatives) may also be used.

In certain embodiments, cellulose may be employed as the first polysaccharide and the second polysaccharide used for forming the dissolvable sponge. Non-limiting examples include carboxy methylcellulose, methylcellulose, ethylcellulose, hydroxypropyl cellulose, hydroxypropyl methyl cellulose and hemicellulose, as well as derivatives thereof including oxidized celluloses. An embodiment well suited for forming the dissolvable sponge incorporates hydroxyethyl cellulose as the first polysaccharide and the second polysaccharide in conjunction with chitosan.

Exemplary cellulosic materials may be obtained from a variety of commercial sources including Dow Wolff Cellulosics (for example, the WALOCEL™ CRT line of sodium carboxymethylcellulose products), Hercules, Inc. (for example, the AQUALON™ line of cellulose gum and carboxymethylcellulose products), Ashland (Natrosol line), and Sigma-Aldrich Co. (for example, No. C4021 microgranular cellulose). The cellulosic material desirably is obtained in particulate form, for example, as free-flowing granules whose average particle diameter is less than about 1 mm, less than about 100 μm, about 1 to about 80 μm, or less than 1 μm.

The number average molecular weights of the polysaccharides are selected to achieve the desired physical characteristics of the dissolvable sponge including but not limited to dry compressive strength, wet compressive strength, dissolution time, hydration time, pore size, and density. The selection of a polysaccharide and its molecular weight provide the ability to control the sponge dry/wet compressive strength, dissolution time, hydration time, pore size, and density by altering the ratio of the high and low molecular weight. Higher molecular weight material may increase these characteristics whereas lower molecular weight material may decrease the characteristics.

The amounts of the components in the combined mixture may be varied to attain desired physical properties of the sponge. For example, the ratio of chitosan and the first and second polysaccharides may be selected to achieve an appropriate mechanical strength and to allow sufficient stenting capability and dissolution rate. The first and second polysaccharide may for example contain about 99% to about 1% of the first polysaccharide and about 1 to about 99% of the second polysaccharide, or about 80 to about 20% of the first polysaccharide and about 20 to about 80% of the second polysaccharide, or about 60% to about 40% of the first polysaccharide and about 40 to about 60% of the second polysaccharide. Overall the mixture of both polysaccharides to chitosan is about 20% to 80% or 80% to 20%.

The dissolvable sponge of this disclosure may further comprise other additives or adjuvants. Non-limiting examples include non-aqueous solvents, acids, bases, buffering agents, antimicrobial agents, therapeutic agents and other adjuvants.

Based upon the selection of chitosan, a first polysaccharide and a second polysaccharide, the disclosed dissolvable sponge may inherently be antimicrobial without requiring addition of a separate antimicrobial agent. A separate antimicrobial agent may be employed if desired. A useful list of such antimicrobial agents may be found, for example, in U.S. Patent Application Publication No. US 2007/0264310 A1. In certain embodiments, the dissolvable sponge when at least partially hydrated possesses an antibacterial effectiveness from time 24 hours through 7 days of at least a 4-log reduction according to the Log Reduction Test. The Log Reduction Test is set forth in the Examples section of this disclosure.

Exemplary therapeutic agents which may be employed in the disclosed dissolvable sponge include any material suitable for use at the intended treatment site including analgesics, anti-cholinergics, anti-fungal agents, antihistamines, steroidal or non-steroidal anti-inflammatory agents, antiparasitic agents, antiviral agents, biostatic compositions, chemotherapeutic/antineoplastic agents, cytokines, decongestants, hemostatic agents (e.g., thrombin), immunosuppressors, mucolytics, nucleic acids, peptides, proteins, steroids, vasoconstrictors, vitamins, mixtures thereof, and other therapeutic materials that will be known to those skilled in the art. A useful list of such therapeutic agents may be found, for example, in the above-mentioned U.S. Patent Application Publication No. US 2007/0264310 A1. Therapeutic agents incorporated in certain embodiments may remain active over at least 14 days when hydrated with steroids. Therapeutic agents remain active throughout the dissolution time of the sponge (ie at least 14 days).

Other adjuvants that may be included in the disclosed rehydratable gel composition and sponge include dyes, pigments or other colorants (e.g., FD & C Red No. 3, FD & C Red No. 20, FD & C Yellow No. 6, FD & C Blue No. 2, D & C Green No. 5, D & C Orange No. 4, D & C Red No. 8, caramel, titanium dioxide, fruit or vegetable colorants such as beet powder or beta-carotene, turmeric, paprika and other materials that will be known to those skilled in the art); indicators; flavoring or sweetening agents including but not limited to anise oil, cherry, cinnamon oil, citrus oil (e.g., lemon, lime or orange oil), cocoa, eucalyptus, herbal aromatics (e.g., clove oil, sage oil or cassia oil), lactose, maltose, menthol, peppermint oil, saccharine, sodium cyclamate, spearmint oil, sorbitol, sucrose, vanillin, wintergreen oil, xylitol and mixtures thereof; antioxidants; antifoam agents; and rheology modifiers including thickeners and thixotropes. The disclosed rehydratable gel composition and sponge desirably do not contain ingredients which might potentially harm patient tissues or structures, e.g., mucosal tissues in the nasal or sinus cavities.

The dissolvable sponge is created by mixing chitosan, a first polysaccharide and a second polysaccharide to form a solution. The first polysaccharide has a number average molecular weight of 1.3 million or greater and the second polysaccharide has a number average molecular weight of 500,000 to less than 1.3 million or less than 500,000. The resulting solution has a viscosity of at least 0.05 Pals at a shear rate of 225 l/s and 25° C. Additionally, in certain embodiments, the solution has a solids content of 0.5% by weight or greater to ensure sufficient formation of a sponge with desired mechanical strength. The pH of the solution may be adjusted during the formation of the solution, particularly while adding certain components to enhance solubility. The overall pH of the solution prior to freezing may be finally modified to a level or range of about 4 to about 6 using a conventionally recognized acid or base, such as hydrochloric acid or sodium hydroxide. The solution is then lyophilized (freeze dried) to a temperature sufficient to prevent the formation of large crystals within the sponge. An exemplary temperature range is about −20° C. to −40° C. Conventional lyophilization practices are suitable for forming the dissolvable sponge. Temperature and pressure ranges for lyophilization are typically determined by the freezing point of the solution (i.e., −40° C., at 2255 mT).

In certain embodiments, a lyophilization cycle may include cooling the material to 5° C. (duration 60 min.) followed by ramp cooling down to −3° C. (duration 20 min.). The material is then held at −3° C. for 120 minutes and then ramp cooled down to −40° C. (duration 120 min.) and then finally held at −40° C. (duration 120 min.) until the sponge is dry. There is no dehydrothermal crosslinking of the dissolvable sponge. The dissolvable sponge of this disclosure is not cross-linked. The chitosan interacts with the cellulose via ionic bonding.

The disclosed dissolvable sponge typically will be placed in suitable sealed packaging subject to sterilization prior to shipment to an end user. Suitable forms of ionizing radiation comprise gamma radiation, ultraviolet light, X-rays or E-Beam radiation. Additional property customization may be carried out by using a sterilization procedure such as gamma radiation or electron beam (E-Beam) processing to cause controlled chain scission. Cold ionizing radiation sterilization (e.g., cold E-Beam sterilization) may be employed to limit the degree of chain scission.

The resulting dissolvable sponge exhibits a desired combination of physical properties that enable improved stenting performance over conventional nasal stents and anatomical stents. The dissolvable sponge exhibits one or more of a wet compression strength or a dry compression strength of at least 20 g according to the Compression Test set forth below in the Examples section of this disclosure. In certain embodiments, the wet compression strength or a dry compression strength is at least 40 g, at least 80 g, or at least 100 g according to the Compression Test.

The dissolvable sponge when at least partially hydrated is also mucoadhesive. Various embodiments of the dissolvable sponge may exhibit a mucoadhesive force of at least 20 grams or greater according to the Adhesive Force Test set forth in the Examples section of this disclosure. Other embodiments may exhibit mucoadhesive force of at least 30 grams or greater according to the Adhesive Force Test.

In some embodiments, the dissolvable sponge quickly hydrates and has the capacity to hold a substantial amount of fluid. The dissolvable sponge may exhibit one or more of a complete hydration in water under 30 seconds, or a fluid absorption of greater than 10 times, greater than 20 times or even greater than 30 times its initial dry weight in accordance with the Fluid Absorption Test. The resulting sponge of this disclosure also exhibits a desired dissolution rate that is selectively designed to provide sufficient stenting capability over a targeted time period. Certain embodiment of this disclosure exhibit a dissolution rate of greater than or equal to 1 day according to the Dissolution Test set forth below in the Examples.

The disclosed dissolvable sponge may be hydrated prior to placement or insertion in a treatment site, or may be placed while in a dry state and then hydrated in situ (e.g., via the addition of an externally-supplied hydrating fluid, by the uptake of endogenous fluids, or both). Hydrating the sponge normally is relatively straightforward, and may be carried out by immersing or saturating the sponge with water or an aqueous solution containing any other desired ingredients. For example, normal saline solution may be a preferred and readily available hydration solution, and other materials such as phosphate buffered saline (PBS) may be used if desired.

In those instances where it is desirable to remove water from tissue, e.g., to remove fluid from polyps or edematous tissue, a hyperosmolar agent may be employed in the disclosed hydratable gel composition and sponge. Exemplary hyperosmolar agents include furosemide, sodium chloride gel and other salt preparations that draw water from tissue or substances which directly or indirectly change the osmolar content of the mucous layer. Chitosan HCL, a water soluble chitosan salt formulation, may also provide hyperosmolor functions and its osmolarity is directly related to the concentration in the sponge. The chitosan contained in the sponge provides a hyper osmotic environment for tissue healing. Where sustained release or delayed release of a therapeutic agent is desirable, a release agent modifier may also be included.

The disclosed dissolvable sponge may desirably be used as a part of a multi-step treatment regimen which disrupts a bacterial biofilm and discourages its return. For example, a series of steps that may be broadly classified as Cleansing/Disrupting, Killing, Aerating, Protecting/Coating, and Healing may be carried out. The Cleansing/Disrupting step may be carried out by administering a solvating system. The Killing step may be carried out by applying a suitable antimicrobial agent to the treatment site. This may for example be accomplished by including an antimicrobial agent in the solvating system, as a separately-applied composition, or in both the solvating system and in a separately-applied composition. An antimicrobial agent may also be applied or administered post operatively. The Aerating step may be carried out by providing air passageways or improving air passageways to the treated tissues by opening occluded or partially occluded passages, e.g., the sinuses or sinus ostia for nasal applications. This may for example be accomplished by surgically removing obstructive tissue structures or by manually displacing such structures. The Protecting/Coating step may be carried out by covering at least part of the thus-treated tissue with the disclosed dissolvable sponge. The Healing step may be carried out by allowing the cleansed, protected and sealed tissue surface to undergo a return to a normal state, e.g., through one or more healing mechanisms such as modulation of an inflammatory response, phagocytosis, mucosal remodeling, reciliation or full or partial restoration of normal function. The multi-step treatment regimen may include or be followed by a Clearing step in which the sponge is sufficiently biodegradable, dissolvable, or bioresorbable to disappear from the treatment site in a desired time period, e.g., more than 1 day, more than 3 days, or about 4 to 14 days, and desirably without shedding large solid chunks. The disclosed method may advantageously be accomplished without requiring surgery, for example by applying and removing the optional solvating system through normal aspiration/suction techniques or by simple flushing of affected tissue followed by application of the disclosed gel composition or sponge. A comparable series of steps may be performed in a multi-step treatment regimen in a portion of the middle or inner ear or other anatomical locations. Further details regarding such a regimen may be found in U.S. Patent Application Publication No. US 2007/0264310 A1.

EXAMPLES

Dissolution and Compression Test: The plunger from a 12 ml (Monojet) syringe is removed and a cap placed on the Luer end of the syringe. An 8 cm sponge is cut in half and placed into the open end of the syringe with the sponge pushed down to the bottom. Then about 8 ml of a 1×PBS solution with Lysozyme (1 g/L) is added to the syringe/sponge to hydrate the sponge. The hydrated sponge is then placed into a 37° C. oven until tested. This configuration creates an air/liquid interface that is similar to the interface seen in-vivo in patients. A 10.2 kg load cell is attached to an MTS machine (MTS, Eden Prairie, MN) using a 12 mm spacer block. The program test speed is set to 1 in/min then the top compression platen is lowered until it just touches the top of the spacer block (0 g force). Once the platens are in place, the force and the displacement are both zeroed out. The sponge is removed from the syringe and placed onto the bottom compression platen. The top platen is adjusted downward until the displacement is zero. The sponge should not be touching the top compression platen. The automated program is run at the specified test speed rate and the max compression force (grams) to compress the sample 10 mm is recorded. The force required to compress the sponges over time represents the sponge dissolution time (dissolving away over time). Over time the sponge shall gradually dissolve away into a clear jelly-like substance with no compressive strength and at that point is considered completely dissolved. Depending on the test being performed the sponges can be irrigated with water daily to help facilitate dissolution.

Dry compression testing is conducted using the same technique above but the sponge is not hydrated prior to testing and no syringe or lysozyme solution is used.

Adhesion Force Test: Cut one 8 cm sponge in half and place each half into individual trays and hydrate the sponge with water (8 ml). The samples are then allowed to dry at room temperature overnight. Black soft OO rubber hemispheres (2 inch diameter) are then covered with collagen from sausage casing and placed in an MTS machine. Surface moisture is blotted with a paper towel prior to testing. Excess water on the sponge is removed by blotting with a paper towel. The sponge is placed on the bottom hemisphere and the hemispheres and the sponge are compressed with the MTS machine to a force of 0.45 kg. The adhesive force is then measured by determining the amount of force (grams) needed to separate the top collagen covered hemisphere from the sponge on the bottom hemisphere.

Log Reduction Test: A sponge is subjected to the Log reduction testing by following the USP method #190660 Chapter 51. Three bacterial strains were used: *Eshcherichia coli*: ATCC 25922, *Pseudomonas aeruginosa*: ATCC 9027, and *Staphylococcus aureus*: ATCC 25923. The example is hydrated with 5.0 ml of sterile saline prior to inoculation. The culture medium was soybean casein digest broth. The inoculum carrier is saline T, the growth medium is Tryptic Soy Agar and the neutralizer is Dey-Engley Broth. The antibacterial effectiveness of the sponge is reported as time to achieve a specific log reduction value.

Fluid Absorption Test: The fluid absorption test is conducted by weighing a dry sponge sample (8 cm long sponge cut in half to provide a 4 cm test sample). The sponge is then submerged in water until fully hydrated. The time to fully hydrate the sponge is then measured and recorded. The fully hydrated sponge is then weighed. The sponge fluid absorption is determined by dividing the fully hydrated sponge weight by the dry sponge weight.

Materials

| Material | Supplier |
| --- | --- |
| chitosan hydrochloride | Heppe Medical Chitosan GmbH, Halle, Germany |
| hydroxyethyl cellulose (HEC) (High Molecular Weight~1.3M) | Sigma-Aldrich Co., St. Louis, MO |
| hydroxyethyl cellulose (HEC) (Medium Molecular Weight~750k) | Ashland Inc. Covington, KY |
| phosphate buffered saline solution | Sigma-Aldrich Co |
| Lysozyme | Sigma-Aldrich Co |
| sodium hydroxide | Thermo Fisher Scientific, Boston, MA |
| hydrochloric acid | Thermo Fisher Scientific |

Example 1: Dissolving Sponge Formation

About 4.8 grams of hydroxyethyl cellulose having a molecular weight of ~750 k and about 3.2 grams of a hydroxyethyl cellulose having a molecular weight of ~1.3M were placed into a beaker and thoroughly mixed. About 350 ml of water was then added to the beaker with the hydroxyethyl cellulose. The mixture was then heated to a temperature of about 30-40° C. using a hot plate and an overhead mixer with a paddle attachment run at about 100-150 RPM for 1.5-2 hours until the material was clear (not cloudy) and all clumps were fully dissolved. The pH of the hydroxyethyl cellulose solutions was then adjusted to 3-4 using hydrochloric acid. Separately, about 2 grams of chitosan HCL was placed in a beaker with about 50 ml water added thereafter. The chitosan hydrochloride solution was mixed using a stir plate with mixing rod until the chitosan HCL completely dissolved and was yellow in color. The chitosan solution was then added into the hydroxyethyl cellulose solution while stirring at 100-150 RPM and then mixed for 15-20 min to assure a complete mixing of the two solutions. The pH was adjusted to a value of about 5 using sodium hydroxide. The material was allowed to rest for several hours until the bubbles were removed and the material was clear and free of clumps. The resulting solution was poured into aluminum molds (8 cm×1.5 cm×1.5 cm) and covered with an aluminum plate to prevent ridges and produce a smooth surface. The aluminum molds were then placed in a freezer at approximately −20° C. until the solution was frozen. The resulting frozen material was then lyophilized at −50° C. and about 0.05 torr vacuum for 72 hours to form sponges. The sponges were then removed from the molds in the aluminum plate and packaged for gamma sterilization (33-40 kGy) or E-beam sterilization (22.5-27.5 kGy). The sponges were evaluated according to the Dissolution and Compression Test, Adhesive Force Test, and the Log Reduction Test.

Examples 2-6: Effect of Solution Viscosity on Sponge Formation

The initial solution produced in accordance with Example 1, having 2.5% solids was then diluted (by 50%) from 2.5% to 1.25%, 0.625%, 0.3125%, 0.151%, and 0.0756% to form Examples 2-6. The solutions were then formed into sponges in the same method noted above manner recited in Example 1. The sponges were formed with solids content of 0.5% by weight or greater and viscosity of 0.05 or greater. The viscosity, weight percent solids and the sponge quality are reported in Table 2. Examples 4, 5, and 6 (Table 2) did not form a solid sponge.

TABLE 2

| Dilution Example | Viscosity (@225 1/s) | Weight % (Solids) | Sponge Quality |
|---|---|---|---|
| 1 | 1.405 | 2.5 | Good Sponge |
| 2 | 0.2553 | 1.25 | Good Sponge |
| 3 | 0.05285 | 0.625 | Good Sponge |
| 4 | 0.01345 | 0.3125 | No Sponge |
| 5 | 0.008495 | 0.151 | No Sponge |
| 6 | 0.006185 | 0.0756 | No Sponge |

Examples 7-9: Adhesive Force Test

Sponges produced in accordance with Example were cut in half and placed into individual trays (½ sponges) and hydrated with water (8 ml). The sponges were allowed to dry at room temperature overnight. The sponges were then subjected to the Adhesion Force Test. The results, reported in Table 3, indicate that the hydrated sponge is mucoadhesive with an average adhesive force of 37 grams-force.

TABLE 3

| Example | Adhesive Force (gf) |
|---|---|
| 7 | 28.542 |
| 8 | 44.204 |
| 9 | 39.068 |

Example 10: Dissolution Test Using Therapeutic Agents

Figure 3:
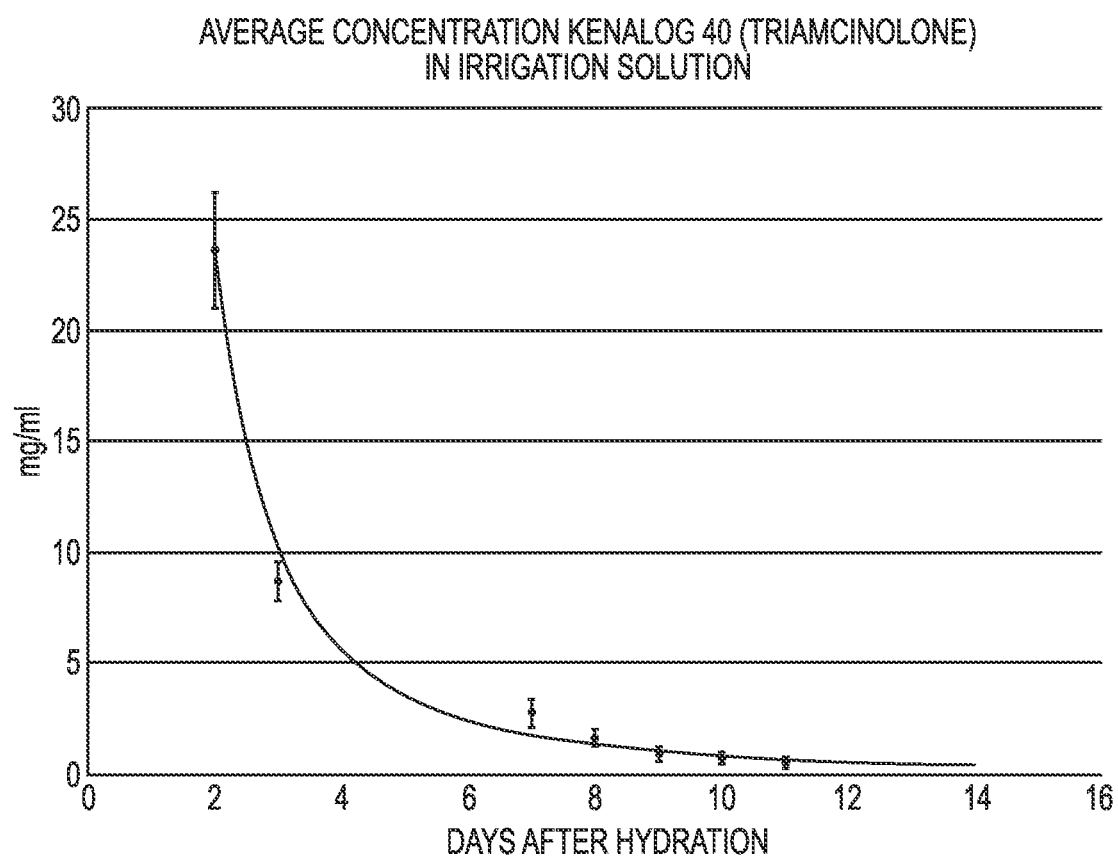
FIG. 3 is a graph depicting the presence of a therapeutic agent over time in an embodiment of this disclosure.

A therapeutic agent was used to hydrate a sponge produced according to Example 1 and the sponge was evaluated in accordance with the Dissolution Test noted above. The topical steroid Triamcinolone (the active ingredient in the steroid Kenalog-40) was used to hydrate a sponge produced according to Example 1 above. The Triamcinolone replaced water/saline for the Dissolution Test noted above. The results, depicted in FIG. 3 indicate that the sponge dissolved away within 14 days. In addition, FIG. 3 shows that the drug present in the irrigation solution remains in the sponge throughout the dissolution time and slowly elutes out of the sponge over time.

The average drug concentration was evaluated using a validated HPLC method and a Zorbax Eclipse XDB-C18 "Agilent", Analytical 4.6×150 mm, 5 μm, PN 993967-902, SN USKH031027 column, along with a Zorbax Diol PN 820950-911, 4.6×12.5 mm, 4 μm Guard Column. The HPLC method was validated for linearity across the test concentration range (88 μg, 44 μg, 22 μg, 11 μg, 5.5 μg, Results $R^2=0.99$), repeatability over 5 different concentrations with 3 replicates each Results $R^2=0.9$, intra-day precision with 5 concentrations and 3 replicates (Results $R^2=0.9$), a test range from 88 μg/ml to 5.5 μg/ml (target dosage 40 μg/ml), and an accuracy of greater than 80%.

Examples 11-13: Log Reduction Test Results

Sponges produced according to Example 1 were subjected to the Log Reduction Test procedure. The results are reported in Table 4.

TABLE 4

| Organism: *Escherichia coli* ATCC 25922 | | |
|---|---|---|
| Example 11 | Recovered CFU/Example | Log Reduction |
| Initial Contact Time | $2.4 \times 10^6$ | |
| 24 Hour Contact Time | $1.5 \times 10^2$ | 4.2 |
| 3 Day Contact Time | $<1.0 \times 10^1$ | >5.4 |
| 7 Day Contact Time | $<1.0 \times 10^1$ | >5.4 |
| Organism: *Pseudomonas aeruginosa* ATCC 9027 | | |
| Example 12 | Recovered CFU/Example | Log Reduction |
| Initial Contact Time | $2.4 \times 10^6$ | |
| 24 Hour Contact Time | $<1.0 \times 10^1$ | >5.4 |
| 3 Day Contact Time | $<1.0 \times 10^1$ | >5.4 |
| 7 Day Contact Time | $<1.0 \times 10^1$ | >5.4 |
| Organism: *Staphylococcus aureus* ATCC 25923 | | |
| Example 13 | Recovered CFU/Example | Log Reduction |
| Initial Contact Time | $1.3 \times 10^6$ | |
| 24 Hour Contact Time | $<1.0 \times 10^1$ | >5.1 |
| 3 Day Contact Time | $<1.0 \times 10^1$ | >5.1 |
| 7 Day Contact Time | $<1.0 \times 10^1$ | >5.1 |

Example 14: Fluid Absorption Test Results

The fluid absorption test was conducted with a sponge produced according to Example 1. The Example exhibited a complete hydration in water under 30 seconds and a fluid absorption of greater than 34 times its initial dry weight.

Although specific embodiments have been illustrated and described herein for purposes of description of the preferred embodiments, it will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

What is claimed is:

1. An article, comprising:
   a water-absorbent, porous, dissolvable sponge derived from a mixture of polysaccharides consisting of chitosan and a plurality of cellulosic polysaccharides, and optionally one or more other polysaccharides distinct from chitosan, the plurality of cellulosic polysaccharides having different number average molecular weights enabling control of mechanical features of the dissolvable sponge to form a sponge that is hydratable, has stenting capabilities to hold open an anatomical location, and exhibits a wet or dry compression strength of at least 20 grams according to the Compression Test and a dissolution rate of greater than or equal to 1 day according to the Dissolution Test.

2. The article according to claim 1, wherein the dissolvable sponge is degradable by mechanical dissolution or chemical dissolution.

3. The article according to claim 1, wherein the dissolvable sponge when partially hydrated is mucoadhesive and exhibits a mucoadhesive force of 20 grams or greater according to the Adhesive Force Test.

4. The article according to claim 1, wherein the dissolvable sponge begins to dissolve upon hydration.

5. The article according to claim 1, wherein the dissolvable sponge exhibits one or more of a wet compression strength or a dry compression strength of at least 100 grams according to the Compression Test, or a dissolution rate of greater than or equal to 1 day according to the Dissolution Test.

6. The article according to claim 1, wherein the dissolvable sponge when partially hydrated possesses an antibacterial effectiveness from 24 hours to over 14 days with a log reduction of 4 according to the Log Reduction Test.

7. The article according to claim 1, wherein one or more of the plurality of cellulosic polysaccharides and other polysaccharides include cellulose, agar, alginate, carrageenan, chitin, chondroitin sulfate, dextran, galactomannan, glycogen, hyaluronic acid, starch or a combination thereof.

8. The article according to claim 7, wherein the cellulose includes hydroxypropyl cellulose, hydroxyethyl cellulose, hydroxypropyl methyl cellulose, hydroxymethyl cellulose, or carboxymethyl cellulose.

9. The article according to claim 1, wherein one or more of the plurality of cellulosic polysaccharides and other polysaccharides include hydroxyethyl cellulose.

10. The article according to claim 1, wherein the dissolvable sponge is a nasal sponge employed for holding open a nasal passage.

11. The article according to claim 10, wherein the nasal sponge prevents adhesion of tissue in the sinus cavity.

12. The article according to claim 1, wherein the chitosan is chitosan hydrochloride.

13. The article according to claim 12, wherein the dissolvable sponge is antimicrobial.

14. The article according to claim 1, further comprising an adjuvant selected from the group consisting of non-aqueous solvents, acids, bases, buffering agents, antimicrobial agents and therapeutic agents.

15. The article according to claim 14, wherein a portion of the therapeutic agent is present in the dissolvable sponge over time until the dissolvable sponge exhibits no compressive strength, as determined in accordance with the Dissolution and Compression Test.

16. The article according to claim 1, wherein the dissolvable sponge is sterilized by ionizing radiation.

17. The article according to claim 1, wherein the dissolvable sponge exhibits one or more of a complete hydration in water under 30 seconds, or a fluid absorption of greater than 10 times over its initial dry weight in accordance with the Fluid Absorption Test.

18. The article according to claim 1, wherein the sponge possesses a pH value in the range of about 4 to about 6.

19. The article according to claim 1, wherein the dissolvable sponge begins to dissolve upon immersion in an aqueous solution containing saline or phosphate buffered saline.

20. The article according to claim 1, wherein a hyperosmolar agent is further employed in connection with the dissolvable sponge and is configured to draw water from tissue to change the osmolar content of the mucous layer.

\* \* \* \* \*